US00PP22744P2

(12) United States Plant Patent
Brotzman

(10) Patent No.: US PP22,744 P2
(45) Date of Patent: May 22, 2012

(54) ***CERCIS* PLANT NAMED 'VANILLA TWIST'**

(50) Latin Name: *Cercis canadensis*
Varietal Denomination: VANILLA TWIST

(76) Inventor: Timothy Charles Brotzman, Madison, OH (US)

( * ) Notice: Subject to any disclaimer, the term of this patent is extended or adjusted under 35 U.S.C. 154(b) by 0 days.

(21) Appl. No.: 12/928,953

(22) Filed: Dec. 24, 2010

(51) Int. Cl.
*A01H 5/00* (2006.01)

(52) U.S. Cl. ..... Plt./216

(58) Field of Classification Search ..... Plt./216
See application file for complete search history.

*Primary Examiner* — Annette Para

(57) ABSTRACT

A new variety of *Cercis canadensis* plant named 'VANILLA TWIST' which is characterized by weeping habit, light green leaves and white flowers. In combination, these characteristics distinguish 'VANILLA TWIST' from all other cultivars known to the inventor.

2 Drawing Sheets

Genus: *CERCIS*.
Species: *canadensis*.
Denomination: 'VANILLA TWIST'.

BACKGROUND OF THE INVENTION

The present invention relates to a new and distinct cultivar of *CERCIS canadensis*, commonly known as Redbud or Eastern Redbud, which is grown as an ornamental tree for use in the home garden and commercial landscapes. The new cultivar is known botanically as *CERCIS canadensis*, and will be referred to hereinafter by the cultivar name 'VANILLA TWIST'. 'VANILLA TWIST' has resulted from a breeding program which the inventor has carried out in Madison, Ohio since 1998 with the aim of producing new and improved varieties of *CERCIS*.

'VANILLA TWIST' was developed and selected by the inventor as follows: First, the inventor assembled in a pollination cage plants of the two varieties *Cercis* 'Covey' and *Cercis* 'Royal White'. *Cercis* 'Covey' (U.S. Plant Pat. No. 10,328) was selected by the inventor and is known for its strongly arching and pendulous habit. *Cercis* 'Royal White' is an unpatented selection which is known for its abundant white flowers and for its cold tolerance. Pollination was effected by the introduction of bees and seed was collected from plants of both parent varieties. From this first generation seed, the inventor raised seedlings which were grown on to flowering and then exposed to the same pollination process. The second generation seed was collected and seedlings were raised and transplanted into the field for evaluation. In 2008, the inventor selected one seedling, 'VANILLA TWIST' for its combination of cold tolerance, white flowers and pronounced weeping habit of all of its branches. In addition, the leaves of 'VANILLA TWIST' do not exhibit at any stage of growth the reddish anthocyanin pigmentation which characterizes non-white flowered cultivars and seedlings of *CERCIS* including the parent variety 'Covey'.

'VANILLA TWIST' is the only variety of *Cercis* known to the inventor which combines a weeping or arching habit with white flowers. In more detail, 'VANILLA TWIST' may be compared with its parents and with other varieties of *Cercis* known to the inventor as follows:

In addition to 'VANILLA TWIST', the following varieties of *Cercis* exhibit a weeping or arching habit but none bears white flowers: (a) the parent variety, 'Covey' which bears green leaves and lavender-purple flowers, (b) *Cercis* 'Ruby Falls' (U.S. Plant Pat. No. 22,097) which bears deep purple foliage and bright purple flowers, (c) *Cercis* 'Pink Heartbreaker' (U.S. Plant Patent Pending) which bears green leaves and pink flowers, (d) *Cercis* 'Whitewater' (U.S. Plant Patent Pending) which bears variegated (green-cream) foliage, (e) *Cercis* 'Cascading Hearts Falls' (U.S. Plant Pat. No. 18,528) which bears green foliage and purple-pink flowers, and (f) *Cercis* 'Traveler' (U.S. Plant Pat. No. 8,640) which is a selection of *Cercis canadensis* var. *texensis* and which bears glossy dark green foliage and rose-pink flowers.

In addition to 'VANILLA TWIST', the following varieties of *Cercis* exhibit white flowers but none exhibits a weeping or arching habit: (a) the parent variety, 'Royal White' which is renowned for its cold hardiness and which bears green leaves and has an upright habit, (b) *Cercis* 'Alba' (unpatented) which bears green leaves and has an upright habit, and (c) *Cercis canadensis* 'Dwarf White' (unpatented) which if upright but grows only to 7 feet in height after ten years, and (d) *Cercis canadensis* var. *texensis* 'Texas White' (unpatented) which is upright with green leaves and white flowers.

SUMMARY OF THE INVENTION

The distinguishing characteristics of 'VANILLA TWIST' are as follows: In combination these traits set 'VANILLA TWIST' apart from all other existing varieties of *CERCIS* known to the inventor. 'VANILLA TWIST' has not been tested under all possible conditions and phenotypic differences may be observed with variations in environmental, climatic, and cultural conditions.

1. The branches of 'VANILLA TWIST' exhibit a weeping habit
2. The leaves of 'VANILLA TWIST' are light green in color.
3. The leaves of 'VANILLA TWIST' do not exhibit any anthocyanin pigmentation.
4. The flowers of 'VANILLA TWIST' are white in color.

5. After one year of growth, 'VANILLA TWIST' achieves a height of 6 feet to 7 feet (1.8 m-2.2 m).

DESCRIPTION OF THE DRAWINGS

The accompanying color drawing illustrates the distinguishing characteristics of 'VANILLA TWIST', namely its pronounced weeping habit and the white color of its buds and flowers.

The drawing labeled

The drawing labeled

DETAILED BOTANICAL DESCRIPTION

Figure 1:
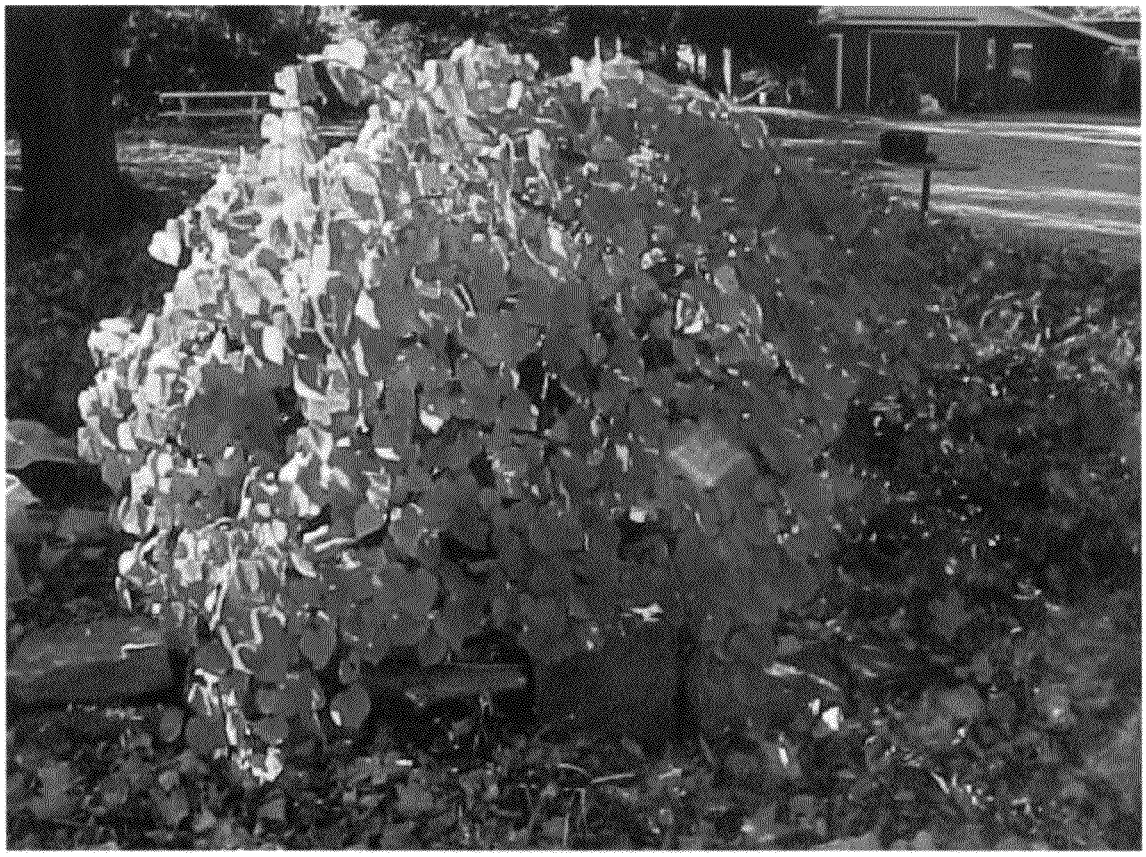
FIG. 1 depicts the early summer growth of a five year old plant of 'VANILLA TWIST' which is growing in open ground at the inventor's nursery in Madison, Ohio.
Figure 2:
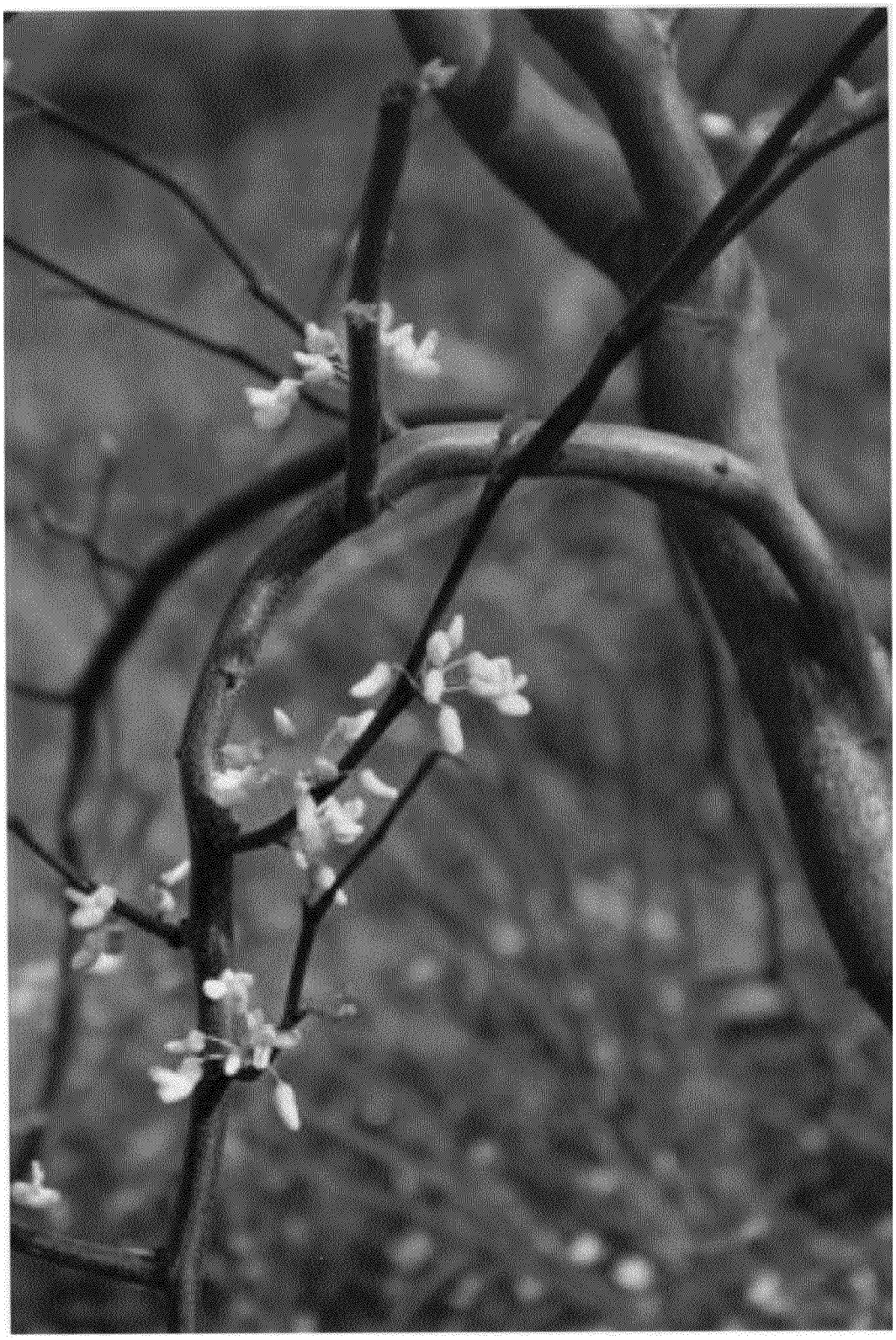
FIG. 2 depicts the arching and pendulous branching of 'VANILLA TWIST'. This drawing also depicts the white buds and flowers of 'VANILLA TWIST' which occur in spring and prior to leafing out.

The following is a detailed botanical description of the new and distinct variety of *Cercis canadensis* known as 'VANILLA TWIST' based upon observation of a five year old specimen tree which is growing at the inventor's nursery in Madison, Ohio.

'VANILLA TWIST' has not been observed under all possible environmental conditions. Where dimensions, sizes, colors and other characteristics are given, such characteristics are approximations or averages set forth as accurately as practicable. The phenotype of the variety may differ from the descriptions set forth herein with variations in environmental, climatic and cultural conditions.

The color determinations have been made by reference to the 2001 edition of The Royal Horticultural Society Colour Chart except where general color terms of ordinary dictionary significance are used.

Family: Fabaceae.

Botanical classification:

*Genus.*—*Cercis.*

*Species.*—*Canadensis.*

Variety denomination: 'VANILLA TWIST'.

Common name: Eastern Redbud.

Use: Specimen tree.

Cultural requirements: Well-drained soils. Drought tolerant.

Light requirement: Full sun or partial shade.

Parentage: 'VANILLA TWIST' is a second generation seedling resulting from the open pollination between parents which the inventor had previously developed by open pollination between *Cercis canadensis* 'Covey' and *Cercis canadensis* 'Royal White'.

Plant description:

*Bloom period.*—March to April depending on location.

*Plant habit.*—Small tree lacks apical dominance and will form a large, mounding shrub or small, twisting tree. Branches are strongly pendulous and will in time touch and run along the ground.

*Vigor.*—Vigorous.

*Dimensions at five years.*—Approximately 2.3 m in height, 1.5 m in width.

*Hardiness.*—USDA Zones 5.

*Root system.*—Fibrous.

*Propagation.*—Budding or grafting.

*Disease and pest resistance or susceptibility.*—No less or more resistant or susceptible to pests or diseases than the species or other cultivars of the species known to the inventor.

Trunk:

*Shape.*—Contorted.

*Dimensions.*—Height 2.3 m, diameter 5.5 cm at 15 cm above ground level.

*Bark surface.*—Smooth, becoming scaly with age.

*Color.*—Newly-formed bark 201A, becoming and remaining 202C with age.

*Lenticels.*—Numerous, tiny. Dimensions: 1 mm or less in diameter. Shape and aspect: Circular. Color: 165B.

Branches:

*Arrangement.*—Lateral branches emerge at 90 to 45 degree angles, become strongly arching and pendulous. Successive year's growth often reverses direction by up to 180 degrees and grows back over itself, creating a twisted or knotted appearance.

*Color.*—200B.

*Branch surface.*—Smooth.

*Dimensions.*—Primary branches: Diameter 2.5 cm. Secondary branches: Diameter 7 mm. Twigs: Diameter 3 mm.

*Internode distance.*—Approximately 2 cm to 6 cm, depending on vigor.

Foliage:

*Type.*—Deciduous.

*Arrangement.*—Alternate.

*Leaf.*—Shape: Broadly ovate. Margins: Entire. Apex: Acute. Base: Cordate. Surface texture (adaxial): Smooth and semi glossy. Surface texture (abaxial): Smooth. Dimensions: 13 cm in length and 15 cm in width. Color (both surfaces): Emerging growth 144B, then varies with age of leaf from 153D to 7A in the fall. Venation pattern: Reticulate.

*Petiole.*—Color: 178A. Surface: Smooth. Dimensions: 3 cm to 4 cm in diameter.

*Stipules.*—None.

*Fragrance.*—None observed.

Flowers:

*Blooming period.*—Commences in March or April, depending on location and spring climate. Peak bloom in Madison, Ohio is typically during first week of May.

*Number of flowers per cluster.*—4 to 8.

*Type.*—Papillonaceous (pea-like).

*Arrangement.*—Sessile clusters.

*Location.*—Nodes of previous year's growth and along older trunks (cauliflory).

*Length of bloom.*—2-3 weeks.

*Flower dimensions.*—1.3 cm in length measured from keel to standard.

*Petals.*—Number: 5, lower 2 petals fused (collectively referred to as the keel). Standard or banner color: N78B. Keel petal color: N78B. Wing petal color: 77B. Calyx lobe color: N74C. Calyx base: fused. Calyx base color: 71A.

*Buds.*—Dimensions: At base 2 mm to 3 mm in length, and 1 mm to 1.4 mm enlarging to 2.4 mm to 3.5 mm at top. Shape: Broadly oval. Color: 61A. Number: Approximately 4 to 8 per cluster.

*Pedicel dimensions.*—1 cm in length and 2 mm to 3 mm in diameter.

*Pedicel color.*—N74C.

Reproductive organs:

*Stamen number.*—10.

*Stamen dimensions.*—Approximately 4 mm in length, less than 0.5 mm in diameter.

*Pistil number.*—1.

*Pistil dimensions*.—Approximately 5.3 mm to 5.5 mm in length, less than 1 mm in diameter.

Fruit:

*Shape*.—Leguminous.

*Color.*—144A to 177A at maturity.

*Dimensions.*—5 cm to 7 cm in length and 1 cm in width.

*Arrangement*.—Borne along branches in a pendant manner.

The invention claimed is:

1. A new and distinct cultivar of *Cercis canadensis* plant named 'VANILLA TWIST', substantially as described and illustrated herein.

* * * * *